(12) United States Patent
Coppens et al.

(10) Patent No.: US 9,021,632 B2
(45) Date of Patent: May 5, 2015

(54) PATIENT POSITIONING DEVICE PRIMARILY DEVELOPED FOR STEREOTACTIC BODY RADIO SURGERY (SBRT)

(75) Inventors: Daniel D. Coppens, Avondale, PA (US); David M. Rabeno, Avondale, PA (US); Steven M. Fisher, Wilmington, DE (US); John Damon Kirk, Ramsey, NJ (US)

(73) Assignee: QFix Systems, LLC, Avondale, PA (US)

(*) Notice: Subject to any disclaimer, the term of this patent is extended or adjusted under 35 U.S.C. 154(b) by 411 days.

(21) Appl. No.: 12/838,417

(22) Filed: Jul. 16, 2010

(65) Prior Publication Data

US 2012/0011653 A1    Jan. 19, 2012

(51) Int. Cl.
*A47B 13/00* (2006.01)
*A61N 5/10* (2006.01)
*A61B 6/00* (2006.01)
*A61B 6/04* (2006.01)

(52) U.S. Cl.
CPC ............... *A61N 5/1049* (2013.01); *A61B 6/00* (2013.01); *A61B 6/04* (2013.01); *A61N 5/1042* (2013.01); *A61N 2005/1097* (2013.01)

(58) Field of Classification Search
CPC .......... A61B 6/04; A61B 6/032; A61B 6/502; A61B 6/0414; A61B 6/0407; A61B 6/027; A61B 6/0421; A61B 6/035; A61B 6/4441; A61B 6/0435; A61B 6/4417; A61B 5/708; A61B 6/0478; A61G 13/101; A61G 2203/34; A47C 21/00; A47C 21/024
USPC ............... 5/601, 600, 621, 503.1–506.1, 658; 378/209, 208, 20
See application file for complete search history.

(56) References Cited

U.S. PATENT DOCUMENTS

| | | | | |
|---|---|---|---|---|
| 3,759,252 A | * | 9/1973 | Berman | 602/19 |
| 3,778,049 A | * | 12/1973 | Viamonte, Jr. | 5/601 |
| 4,064,401 A | * | 12/1977 | Marden | 5/601 |
| 4,377,161 A | * | 3/1983 | Whitt | 128/200.24 |
| 5,163,430 A | * | 11/1992 | Carol | 600/429 |
| 7,060,046 B2 | * | 6/2006 | Tanaka et al. | 602/33 |
| 2006/0026761 A1 | * | 2/2006 | Falbo | 5/601 |
| 2006/0248647 A1 | * | 11/2006 | Huber | 5/505.1 |
| 2008/0005839 A1 | * | 1/2008 | Kogan et al. | 5/601 |
| 2009/0308400 A1 | * | 12/2009 | Wilson et al. | 128/845 |

* cited by examiner

*Primary Examiner* — Robert G Santos
*Assistant Examiner* — Richard G Davis
(74) *Attorney, Agent, or Firm* — RatnerPrestia

(57) ABSTRACT

The present invention provides a patient positioning device, which enables the latest advances in Stereotactic Radiation Therapy. The geometry, which incorporates at least one window or lateral cut-out, is designed to allow clear treatment access to the patient during non-coplanar treatment regimes through the use of windows or lateral cut-outs. A laterally positionable diaphragm compression device allows the full use of the geometry. The development of a stand-alone device and a couch top insert device allows for a maximum number of protocol methods while minimizing the skin surface radiation dose to the patient.

8 Claims, 5 Drawing Sheets

SBRT Standalone Device

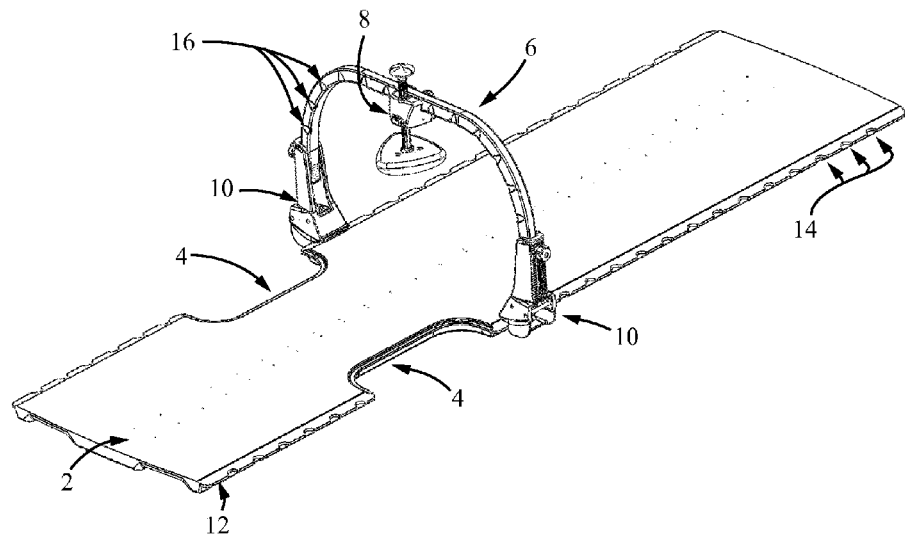
Figure 1: SBRT Standalone Device
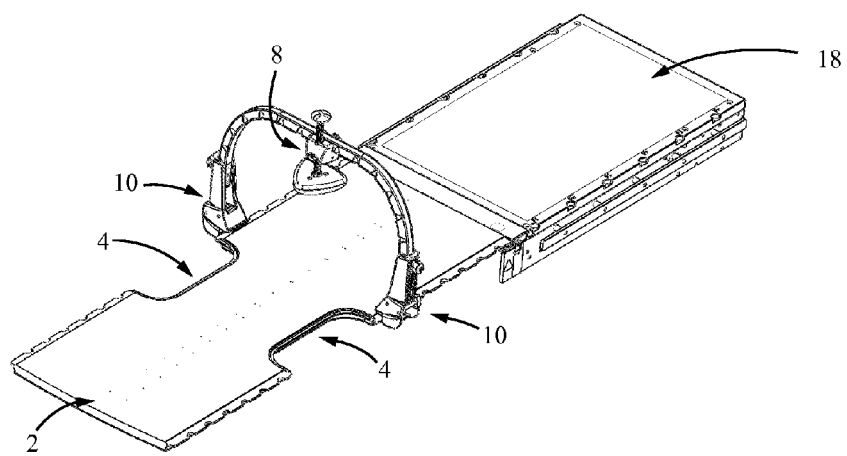
Figure 2: SBRT Couchtop Insert

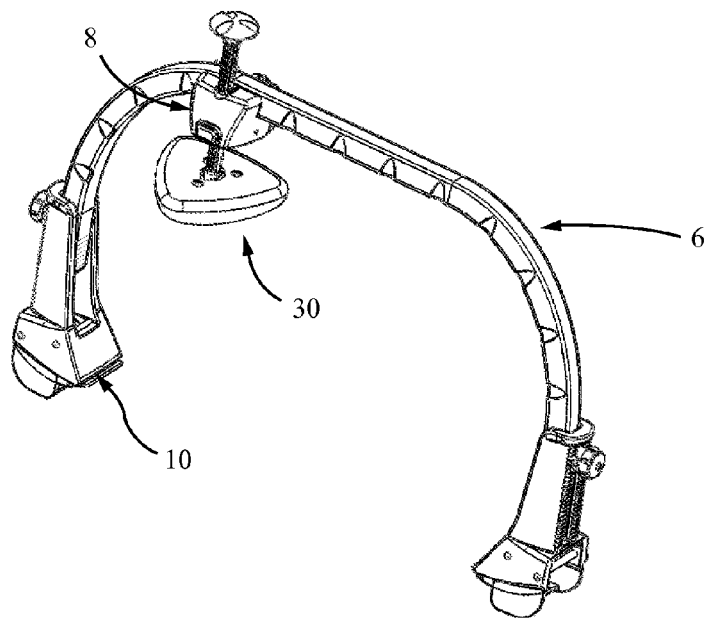
Figure 6(a): Compression Device Shifted to the Left
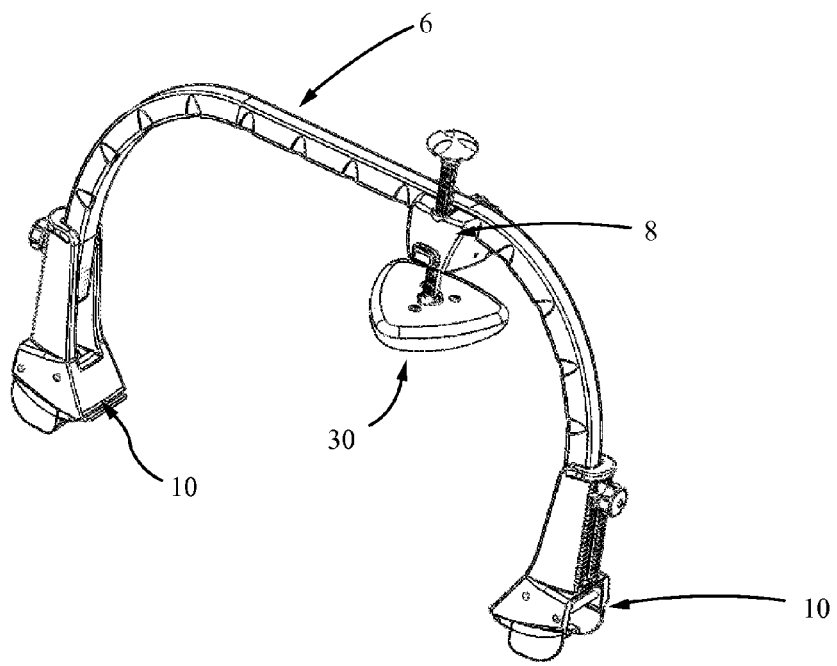
Figure 6(b): Compression Device Shifted to the Right

PATIENT POSITIONING DEVICE PRIMARILY DEVELOPED FOR STEREOTACTIC BODY RADIO SURGERY (SBRT)

BACKGROUND OF THE INVENTION

In the treatment of tumors by radiation therapy, the radiation is often delivered in small doses over many sessions (or fractions). One reason this is done, is to allow the surrounding healthy tissue to tolerate the total radiation dose. Delivering the total dose in many fractions also smoothes out any patient positioning errors which may occur.

The advent of modern computer controlled Radiation Therapy machines such as linear accelerators allows higher doses to be delivered in fewer fractions (often referred to as hypo-fractionation). This kind of treatment regime can be popular with patients due to the reduced time required of the patient for treatment. It can also reduce the cost of healthcare as the treatment times are shorter. However, these kinds of treatment require higher patient positioning accuracy. In addition, due to the need to limit the dose to the healthy tissue, it is desirable to be able to treat with a maximum of beam paths which enter the patient from many directions. This can be accomplished on a modern linear accelerator through the use of VMAT techniques and non-coplanar beam angles. Traditional linear accelerators generally treat in planes which are perpendicular to the patient axis. Through the use of modern computer controls, it is possible to treat in planes that are not perpendicular (coplanar) to the patient axis.

This new capability can be enhanced and enabled through the use of well designed positioning devices. In the present invention, we have developed the ability to allow greater access to the torso so that treatments can be delivered, unimpeded by the positioning devices themselves. This is particularly beneficial in Proton Therapy since the negative impact of treating through the device is even greater than with standard linear accelerator techniques.

SUMMARY OF THE INVENTION

A number of devices exist for the positioning of patients during SBRT treatments. These devices are available commercially and have been produced for internal use by cancer centers. The devices often include a patient support surface and a bridge. The bridge usually located straddles the patient laterally. Attached to the bridge is a compression device in a fixed position which puts pressure on the diaphragm to limit patient breathing. This in turn minimizes the motion of tumors in the lung and other organs of interest such as the liver and pancreas. Treatments of this type generally take place with the patient in the supine position.

The present invention incorporates a pair of lateral cut-outs which allow unimpeded treatment access for posterior and posterior oblique treatment angles. In addition, the present invention provides for an adjustable diaphragm compression device which can slide laterally along the top of the bridge. This allows the patient to be placed off the central axis of the device while still being able to apply the compression device to the center of the diaphragm. For example, for a patient with a tumor in the right lung the patient may be positioned to the right side of the device such that the lung and corresponding tumor are preferentially over the right lateral cutout of the device. The diaphragm compression device is then shifted to the right side of the bridge so that it is centered over the diaphragm. Anterior and anterior oblique treatments can now take place without being affected by the patient support surface.

The instant invention can be employed on any linear accelerator couch top. However, it works particularly well on the kVue™ Couchtop. The kVue™ Couchtop employs laterally sliding support rails so that the rails can be kept out of the treatment field. (EXPAND-cross reference). For example, by placing these in the inner position, unencumbered treatment access is assured. The standalone version of the device works particularly well when used with the Varian Exact® Couchtop for similar reasons.

Positioning of the bridges superiorly and inferiorly is accomplished through the use of a pair of clamps incorporated on either side of the bridge. The device body contains both indexing features and a millimeter scale to provide locating options. The device body itself is produced from composite materials to minimize the effect on the treatment beam in the event that is does travel through the device.

The present invention overcomes the above limitations of the prior art and provides adaptability with modern radiation therapy techniques by incorporating at least one lateral cutout which allow unimpeded treatment access for posterior and posterior oblique treatment angles. In addition, the present invention provides for an adjustable diaphragm compression device which can slide laterally along the top of the bridge thereby accommodating treatment of the patient placed off the central axis of the device while still being able to apply the compression device to the center of the diaphragm.

Specifically, the present invention provides patient support and positioning device for Radiation Therapy and Stereotactic Body Radiation Therapy (SBRT) comprising a removable bridge and a diaphragm compression device. The diaphragm compression device further comprises a rod and a compression paddle, wherein the compression paddle is connected to one end of the rod and wherein the diaphragm compression device is attached to the bridge and can be moved laterally along the bridge. The diaphragm compression device can be locked in any desired position along the bridge and wherein, the rod and compression paddle can be adjusted vertically The instant invention also provides a patient support and positioning device further comprising at least one window cutout in the support device thereby allowing unimpeded access of a radiation therapy treatment beam to a patient so that the treatment beam passes through the window cutout but does not pass through a surface of the support device.

BRIEF DESCRIPTION OF THE DRAWINGS

FIG. 1 illustrates a standalone version of the present invention.

FIG. 2 illustrates the couch top insert version of the present invention.

FIGS. 6(a) and 6(b) show the bridge of the present invention.

DETAILED DESCRIPTION OF THE INVENTION

Figure 3:
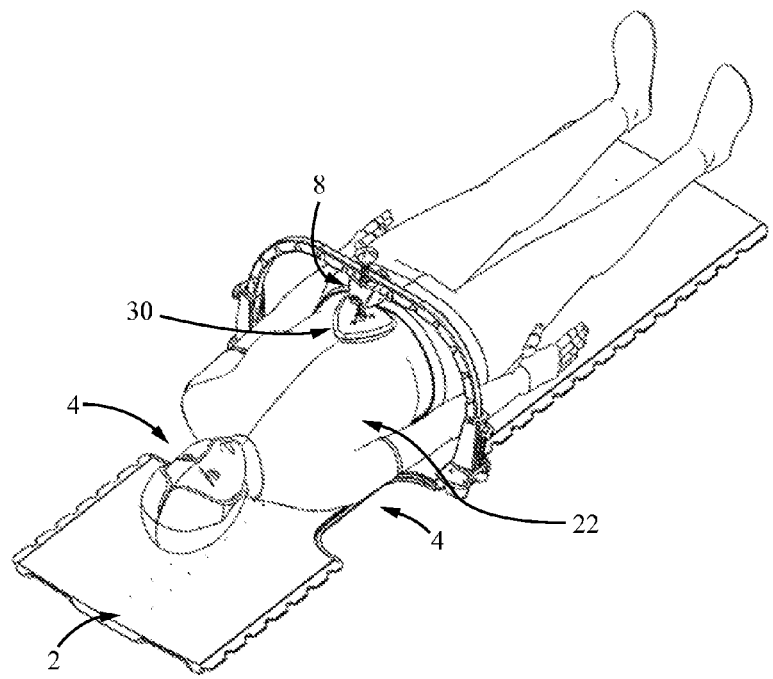
FIG. 3 illustrates the standalone device with patient lying down in the supine position on its central axis.

FIG. 1 depicts a Standalone version of the device. The device body (2) contains a pair of lateral cut-outs (4). As shown in FIG. 1, the lateral cut-outs extend to and form part of the perimeter of the device. The support and position device of the present invention can also have window cut-outs (not shown). The window cut-outs are literally windows cut out of the of the support device and there is a perimeter of support material surrounding the window. The window is substantially free of support material. The window cut-outs can be located as desired on the support device depending on the particular treatment area of the patient. There can be one large window or multiple windows in the support surface. Thus, the treatment beam can proceed through the window in the device into the patient without interference from the support device material. The bridge (6) is attached to the body of the device through a pair of clamps (10) on either side of the bridge. A flange (12) extending from the edge of the device body provides a feature for the attachment of the clamps. The flange also contains standard indexing notches (14). The indexing notches can be used to locate the bridge(s) or any other industry standard positioning device. A millimeter scale is also provided along the length of the flange to allow the bridge to be finely positioned. The diaphragm compression device (8) is also shown attached to the bridge. The compression device can be positioned laterally along the length of the bridge. The location can be varied continuously, or discretely, using the bridge indexing features (16).

FIG. 2 depicts the couch top insert version of the device. The device body (20) insert into the couch top frame (18). In this figure, the device is shown as an insert into the WFR-Aquaplast/Qfix Systems kVue™ Couch Top. The kVue couch top employs laterally sliding support rails (shown in FIG. 5, (26)). This has the added advantage that the support rails can be positioned in the inner position, maximizing the patient access from the posterior direction. Co-pending application Ser. Nos. 11/350,983 and 11/535,055 are hereby incorporated by reference.

Figure 4:
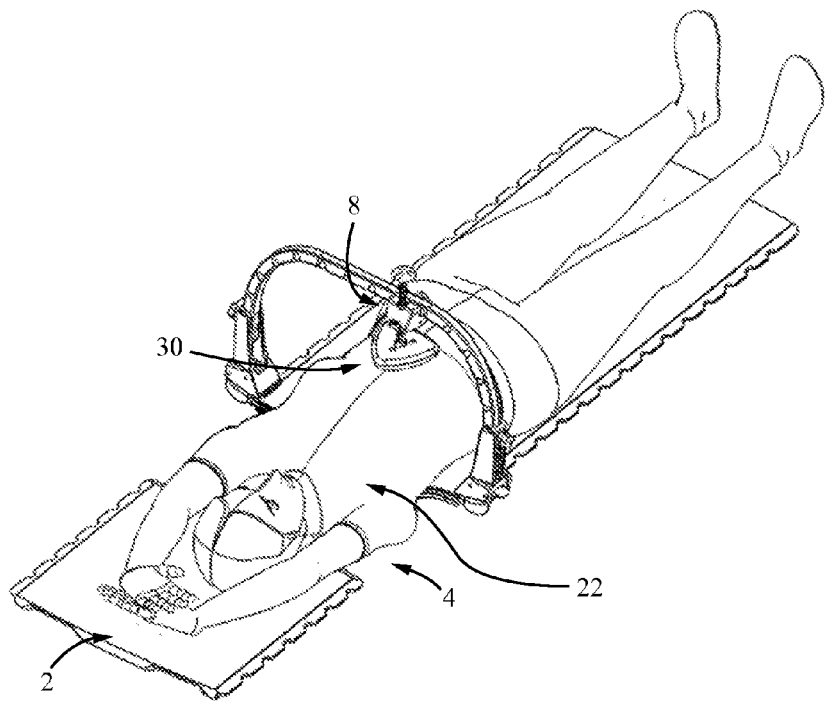
FIG. 4 illustrates the present invention with the patient shifted to the right of the device.

FIG. 3 illustrates the Standalone device with patient lying down in the supine position on its central axis. The compression paddle (30) is placed to apply pressure to the diaphragm, limiting the depth of breathing. In FIG. 4, the patient has been shifted to the right of the device in order to position the lung and superclavicular region over the cut-out (4). The compression device (8) has also been shifted to the right so that it is aligned laterally with the center of the diaphragm.

Figure 5:
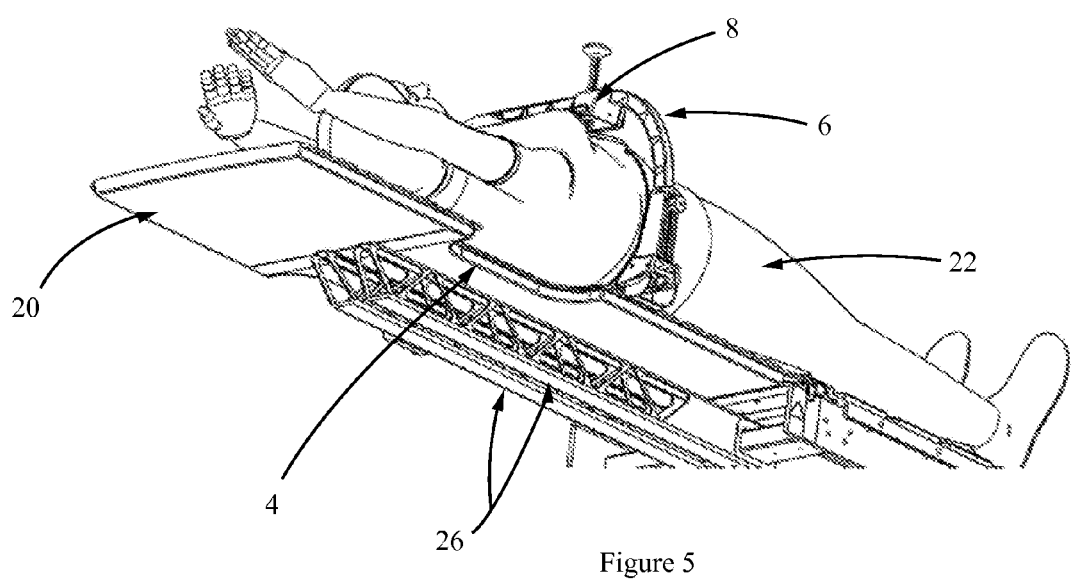
FIG. 5 illustrates a couch top insert version of the present invention from a posterior oblique angle.

FIG. 5 shows a couch top insert version of the device from a posterior oblique angle. The kVue™ support rails (26) are placed in the inner position laterally. The patient (22) is offset to the right side of the device. One can see the excellent treatment access provided.

Figure 7:
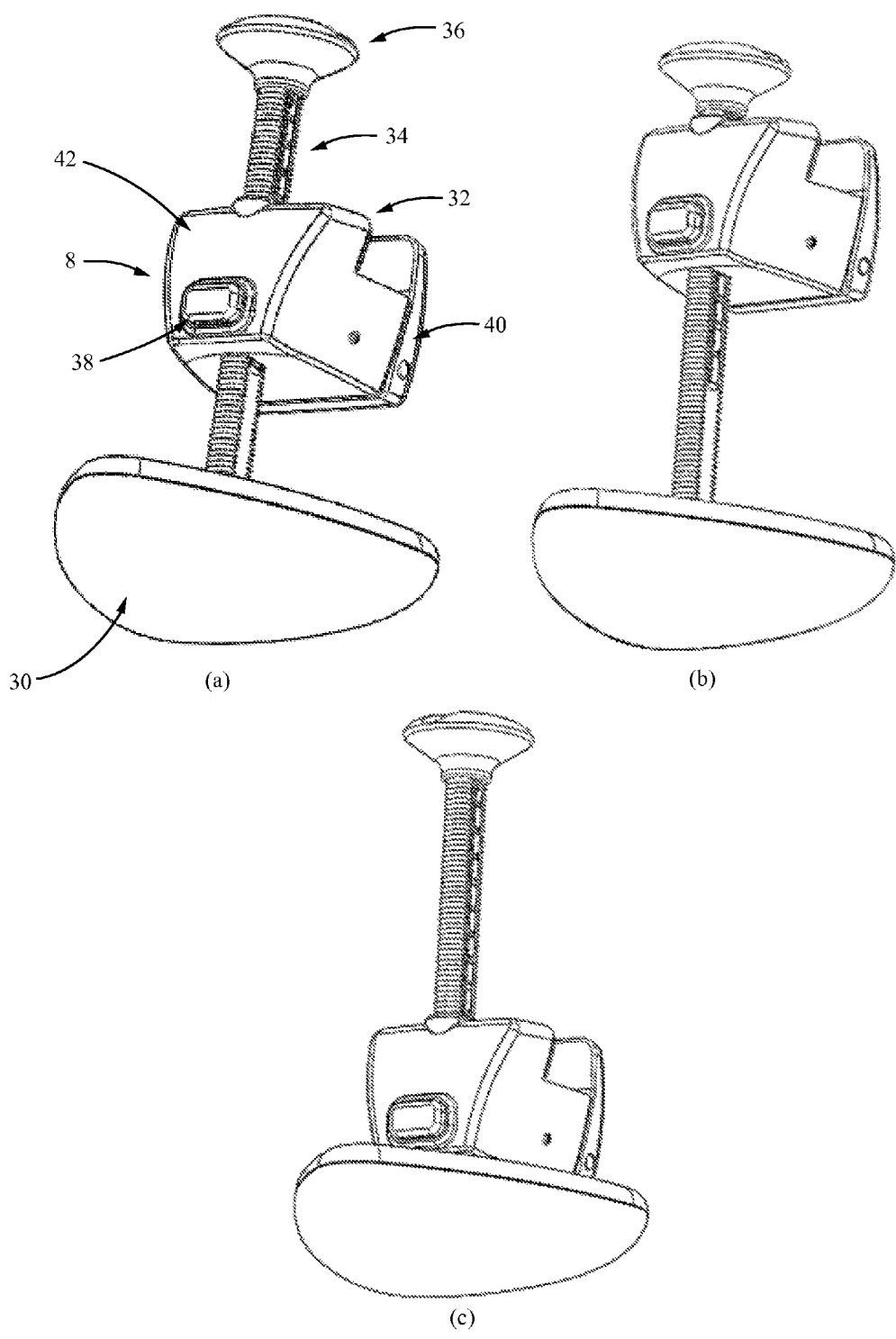
FIGS. 7(a), 7(b), and 7(c) show the compression device in the central, lower and upper positions, respectfully.

FIGS. 6(a) and 6(b) show the bridge by itself. The compression device is offset to the left in FIG. 6(a) and to the right in FIG. 6(b). FIGS. 7(a), 7(b), and 7(c) show the functionality of the compression device (8). In 7(a), 7(b) and 7(c), the compression paddle (30) is shown in the central, lower and upper positions respectively. The compression paddle (30) is softly shaped to maximize patient comfort and breathing control when it impinges on the patient's abdomen. The rod (34) rides up and down in the body (42) the clinician simply pushes down on the palm button (36) and the ratcheting teeth of the rod keep the paddle from returning upward. This arrangement is superior to existing devices because the clinician can fell directly the force being applied to the patent. Other devices use rotary screw motion which reduces the ability of the clinician to feel the patient response. When it is time to release the compression paddle, the button (38) is depressed and the paddle is free to travel upward. The hinged clamp portion (40), moves with respect to the clamp body so that the compression device can be locked to the bridge.

All components of the device are designed so that they can be produced from non-conductive materials so that the device will not interfere with radio frequency systems such as MRI machines and Calypso® localization technology.

The present invention is further defined by the following claims.

We claim:

1. A patient support and positioning device for Radiation Therapy and Stereotactic Body Radiation Therapy (SBRT) comprising a removable bridge, a ratcheting mechanism and a diaphragm compression device, wherein the diaphragm compression device further comprises a rod and a compression paddle, wherein the compression paddle is connected to one end of the rod and a push surface is connected to an opposite end of the rod, and wherein the diaphragm compression device is attached to the bridge and can be moved laterally along the bridge and can be locked in any desired position along the bridge, and wherein the rod and compression paddle can be adjusted vertically with respect to the bridge and independent of adjustment of the bridge; the ratcheting mechanism being positioned to limit relative movement of the rod and the compression paddle with respect to the bridge, wherein the ratcheting mechanism is configured to prevent upward vertical movement of the rod and the compression paddle in response to a force from a body of a patient against which the paddle exerts pressure.

2. The patient support and positioning device of claim 1 further comprising at least one window cutout in the support device thereby allowing unimpeded access of a radiation therapy treatment beam to a patient so that the treatment beam passes through the window cutout but does not pass through a surface of the support device.

3. The patient support and positioning device of claim 1 further comprising at least one lateral cutout that is located at a perimeter of the support device.

4. The patient support and positioning device of claim 1 wherein the bridge further comprises two or more indexing features along a lateral length of the bridge so that an accessory device can be attached at discrete repeatable locations.

5. The patient support and positioning device of claim 1 wherein the diaphragm compression device can be located continuously at any lateral location on the bridge.

6. The patient support and positioning device of claim 1 wherein the diaphragm compression device can be located at discrete repeatable locations along the bridge.

7. The patient support and positioning device of claim 1, wherein the rod and the compression paddle are configured to be adjusted vertically with respect to the bridge by pushing the rod along its axis.

8. The patient support and positioning device of claim 7, further comprising a push button attached to the rod.

* * * * *